United States Patent [19]
Bernardin et al.

[11] Patent Number: 5,602,646
[45] Date of Patent: Feb. 11, 1997

[54] OPTICAL METHOD AND DEVICE FOR AUTOMATICALLY CLASSIFYING CYLINDRICAL NUCLEAR-FUEL PELLETS

[75] Inventors: Michel Bernardin, Claix; Paul Bouvet, Vinay; Claude Wache, Romans, all of France

[73] Assignee: Societe Franco-Belge de Fabrication de Combustibles, Paris, France

[21] Appl. No.: 541,205

[22] Filed: Oct. 12, 1995

Related U.S. Application Data

[63] Continuation of Ser. No. 174,300, Dec. 28, 1993, abandoned.

[30] Foreign Application Priority Data

Dec. 29, 1992 [FR] France .................... 92 15847

[51] Int. Cl.⁶ .................................................. G01N 21/84
[52] U.S. Cl. ........................ 356/426; 356/237; 356/445
[58] Field of Search ............................. 356/426, 237, 356/73, 445, 446, 448, 240, 241, 429–431, 428; 250/562, 572, 223 B; 209/538, 587, 655, 657, 576, 577, 938

[56] References Cited

U.S. PATENT DOCUMENTS

| | | | |
|---|---|---|---|
| 4,162,126 | 7/1979 | Nakagawa et al. | 356/237 |
| 4,226,539 | 10/1980 | Nakagawa et al. | 356/445 |
| 4,410,278 | 10/1983 | Makihira et al. | 356/445 |
| 4,532,723 | 8/1985 | Kellie et al. | 356/237 |
| 5,186,887 | 2/1993 | Yaginuma | 356/426 |

FOREIGN PATENT DOCUMENTS

| | | |
|---|---|---|
| 2461944 | 2/1981 | France . |
| 2667398 | 4/1992 | France . |
| 2252404 | 8/1992 | United Kingdom . |

*Primary Examiner*—Hoa Q. Pham
*Attorney, Agent, or Firm*—Pollock, Vande Sande & Priddy

[57] ABSTRACT

In order to classify cylindrical nuclear-fuel pellets automatically, they are rotated about their axis. A flat beam is focused onto a nominal generatrix of the pellet. The returned light coming from an elongate zone, this being the zone illuminated on a defect-free pellet, is collected. The intensity is detected, point by point, along the zone and the defects are deduced from the variations in the intensity. To this end, the points of each zone are determined in which the intensity of the returned light lies between two adjustable normality thresholds, the transition points are stored in memory, and the limits of each defect and its type are determined by neighborhood analysis.

11 Claims, 3 Drawing Sheets

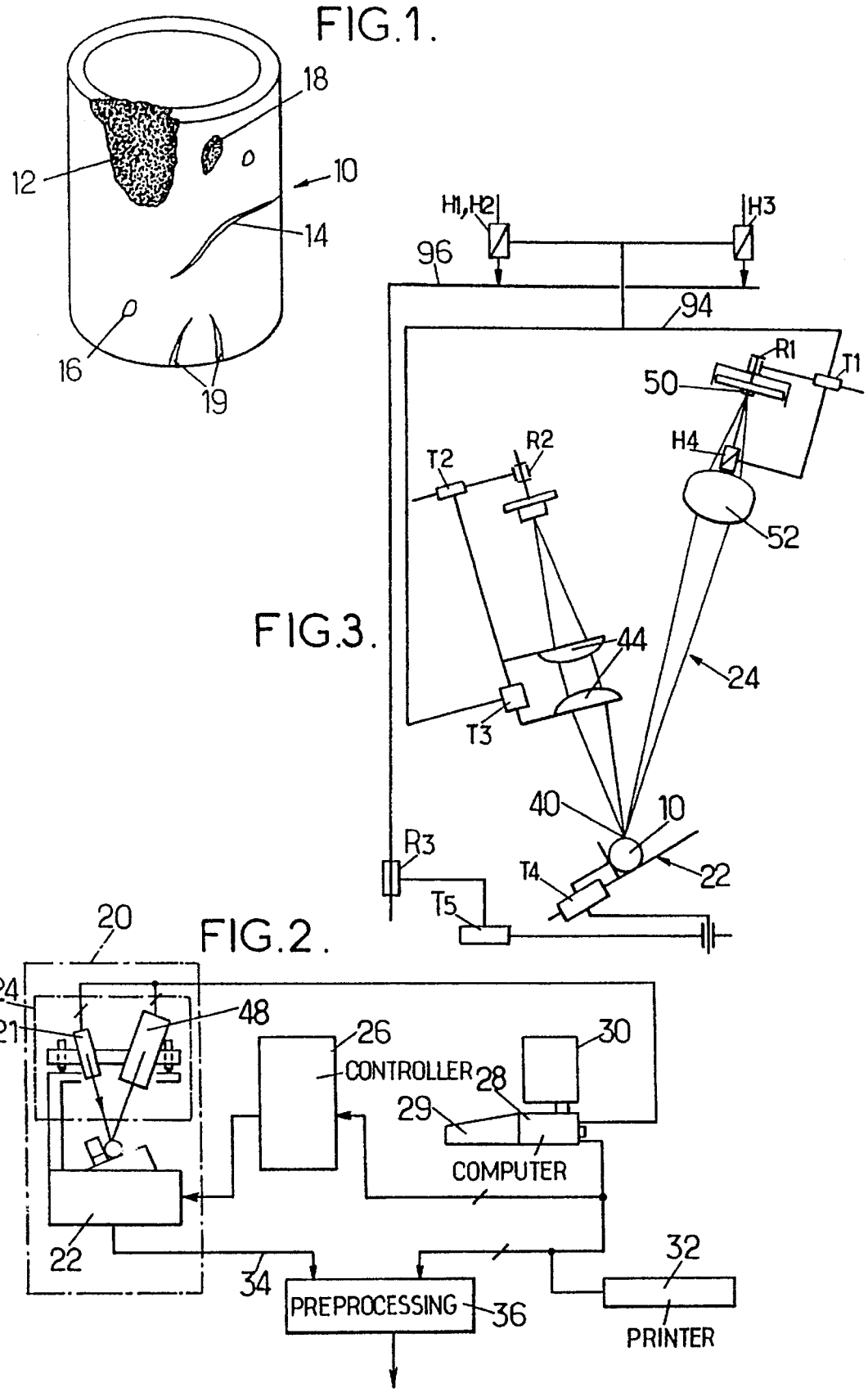

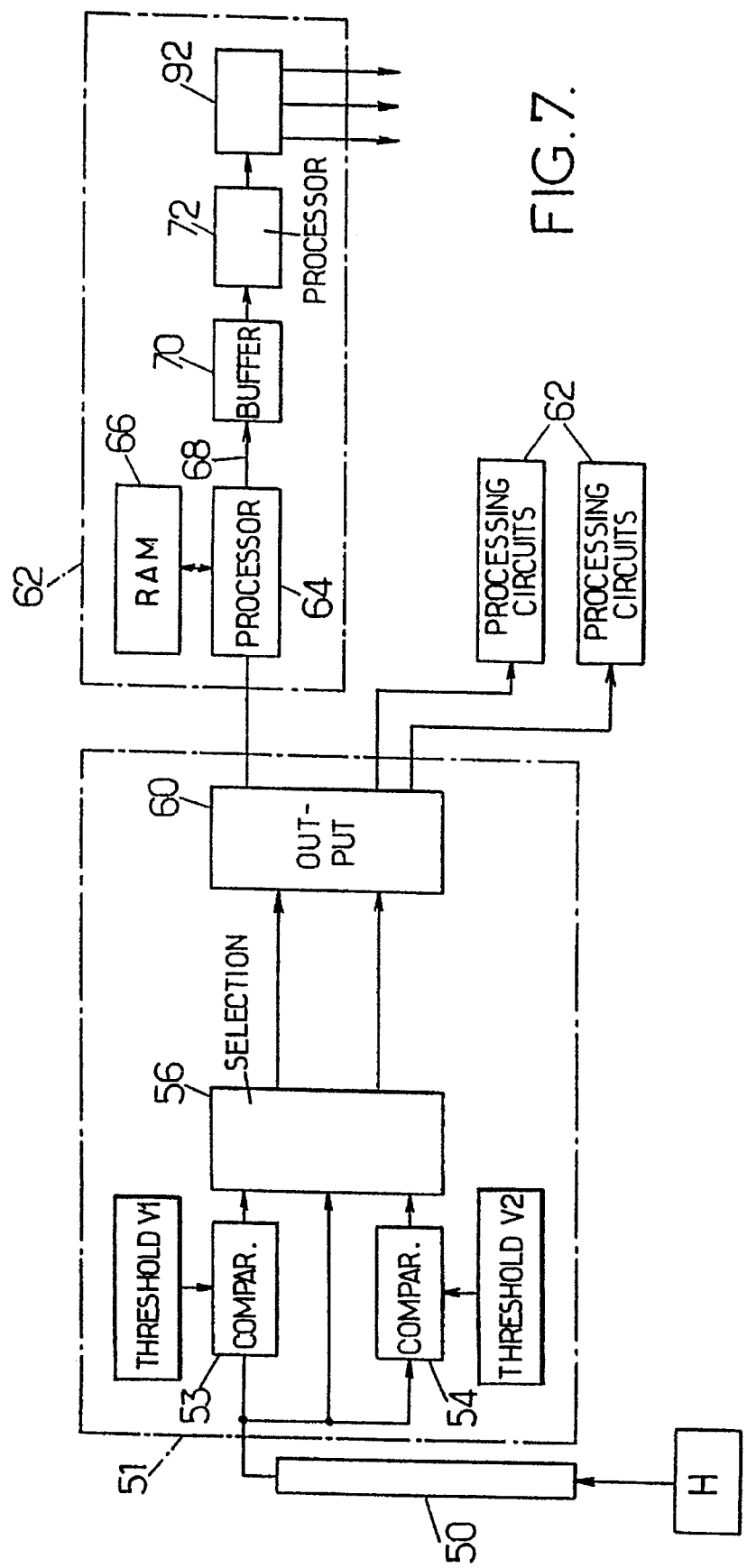

OPTICAL METHOD AND DEVICE FOR AUTOMATICALLY CLASSIFYING CYLINDRICAL NUCLEAR-FUEL PELLETS

CROSS-REFERENCE TO RELATED APPLICATION

This application is a continuation of application Ser. No. 08/174,300 filed Dec. 28, 1993, now abandoned.

BACKGROUND OF THE INVENTION

The present invention relates to the inspection of cylindrical nuclear-fuel pellets (generally based on uranium oxide), which are used in fuel rods for nuclear reactors, with a view to detecting surface defects and to assign the pellets to different classes according to the nature and the significance of the defects which they have.

FIG. 1 shows schematically a nuclear-fuel pellet of the kind used especially in fuel rods of pressurized-water reactors, formed from sintered uranium dioxide, which may contain additional elements and especially, in the case of the reuse of already irradiated fuel, a small amount of fission products and/or of plutonium oxide. The invention may also apply to consumable poison pills, such as those of gadolinium oxide.

A perfect pellet 10 has the shape of a cylinder, the periphery of which is ground and the terminal faces of which have a concave central recess and, possibly, a chamfer. The general appearance of defects liable to be encountered on the lateral face is shown schematically in FIG. 1.

A chip 12 may be caused by a shock during handling; this results in a surface recessed from the theoretical surface.

A crack 14 constitutes a zone of a width very much less than its length, the bottom of which is recessed from the theoretical surface. The combination of several cracks may constitute an ungulate defect 19.

A pit 16 constitutes a surface irregularity characterized by the presence of a ground particle set into the matrix. This particle has the same chemical nature as the pellet.

The abovementioned defects are considered three-dimensional defects. Other types of defect are known, such as, for example, spots, grinding effects and metallic inclusions. A spot is due to soiling of the pellet, arising from the method of manufacture. A grinding defect is a shinier part of the pellet due to an absence of grinding over part of the lateral surface. A metallic inclusion is a part, in general very bright, of the pellet caused by the incrustation of a foreign body in the pellet. Since this foreign body appears at the surface, it is ground and does not constitute a three-dimensional defect. All these defects described here are characterized by different shapes or colors.

Various optical methods for automatically classifying pellets have already been proposed. In particular, FR-A-2, 461,944 discloses a method according to which:

each pellet to be classified is rotated about its axis, a flat beam coming from a light source is focused onto a nominal generatrix of the pellet, the returned light coming from an elongate zone, this zone being that illuminated on a defect-free pellet of nominal diameter, is collected, its intensity is detected, point by point, along the elongate zone, and the defects are deduced from the variations in the intensity.

More specifically, the defects are deduced by comparing the light intensity signal with an average value.

The foregoing method does not allow accurate evaluation of the significance of the defects and leads to rejection or retention of the pellets on the basis of relatively crude criteria. In addition, it is necessary to form two images: the first makes it possible to detect defects such as flaking, a non-ground part, a metallic inclusion; the second makes it possible to detect defects such as cracks, or pits.

SUMMARY OF THE INVENTION

It is an object of the invention to provide a method allowing better evaluation of the nature and of the seriousness of the defects and consequently more refined classification, requiring only a single image to recognize three-dimensional defects and surface defects at the same time.

With this in mind, the invention proposes especially a method of the kind defined hereinabove according to which:

the points of each zone, in which the intensity of the returned light lies between an adjustable upper normality threshold and an adjustable lower normality threshold, are determined, the transition points between a normality region and an abnormality region and the intensity, in digital form, for the points of the abnormality region are stored in memory, the limits of each effect are determined by connexity analysis and the type of defect is determined from among predetermined types identified by geometrical criteria and light-intensity criteria, and the pellets are classified into at least one class of correct pellets and one class of rejected pellets.

The quality requirements relating to the pellets may be different depending on the location in which the pellets are to be placed in a nuclear reactor core. In the zones where the neutron flux is highest, only minimal defects may be tolerated. In other zones in the reactor, the requirements may be less stringent. According to one particularly advantageous embodiment of the invention, the pellet classification step is performed by association into three classes: the first corresponds to the absence of defects or to the presence of acceptable defects without restriction of use, the second corresponds to the presence of defects acceptable in certain parts of the core of the reactor. The third corresponds to the presence of defects which are completely unacceptable by virtue of their significance or their number.

The double-thresholding operation mentioned earlier makes it possible to locate those points which do not correspond to normality; it is not sufficient to identify the defects, nor even the category to which they belong, be it three-dimensional defects or surface-finish defects. This differentiation can especially be performed by new thresholding operations, having threshold levels remote from the normality zone. For example, a three-dimensional defect is manifested by very low intensity of the light collected, less than a low extreme threshold. A highly reflective metallic inclusion at the nominal surface, on the contrary, is manifested by an intensity greater than a high extreme threshold.

The second thresholding operations are advantageously performed, using a software route, on the digitized intensity values, although they may also be carried out on an analog signal.

There is also provided an optical device for automatically inspecting cylindrical nuclear-fuel pellets, comprising: a light source for focusing a beam in the form of a line along a generatrix of a pellet to be inspected; means for rotating the pellet on itself about its axis; a light sensor on which the image of the illuminated generatrix of the pellet is formed by a lens/diaphragm device, the rotation of the pellet allowing all the generatrices of the pellet to be scanned, the device being characterized in that the sensor outputs to a signal processor having:

a preprocessing unit for determining those output signals from the detectors which constitute the sensor and which are outside a normality region defined by an adjustable upper threshold and an adjustable lower threshold, in order to digitize the signals and to register the transitions with the normality region, a processing circuit making it possible to reconstruct the defects, line by line, by comparing each line with the next one and identifying the defects by their shape and their color level and or grey level, means for storing all the defects in memory, as the pellet is being scanned, and for classifying the pellet as a function of predetermined criteria.

In order to permit a high rate of classification, the device is advantageously designed to process several pellets at the same time. In particular, the device may be designed to classify n×m pellets simultaneously, n and m being integers greater than 1. The n×m pellets are rotationally driven simultaneously and in synchronism by the same mechanism and n sensors are provided, each having m×p detectors. A preprocessing circuit assigned to m pellets then performs the comparison with the normality thresholds for the signals supplied by the m×p detectors and subsequently distributes the information collected between n×m processing circuits.

The number of sources may be equal to that of the pellets to be simultaneously classified and may be constituted by laser diodes. The astigmatism of the output beam of these diodes makes it possible to constitute a flat beam highly focused onto a line with the aid of optics consisting of cylindrical lenses. Each sensor may be constituted by a camera having a linear array of CCD detectors, with charge integration over adjustable time periods. The detector may also operate simultaneously with charge storage for the line q of the image and with transfer for the line q-1. This makes it possible to increase the rates. The normality thresholds and the extreme thresholds may be adjusted on the basis of measurements performed on a standard piece.

The invention will be better understood on reading the description which follows of a particular embodiment, given by way of example.

BRIEF DESCRIPTION OF THE DRAWINGS

FIG. 1, is a prespective view of a pellet with surface defects;

FIG. 2 is a schematic representation of the main components of a device according to a particular embodiment of the invention;

FIG. 3 shows schematically the relative arrangement of a pellet in the course of examination, of the source and of the sensor in a device of the kind shown in FIG. 2, as well as a possible distribution of adjustment means;

FIG. 7 is a block diagram of a processor which can be used in a device of the kind shown in FIG. 2.

DETAILED DESCRIPTION

Figure 4:
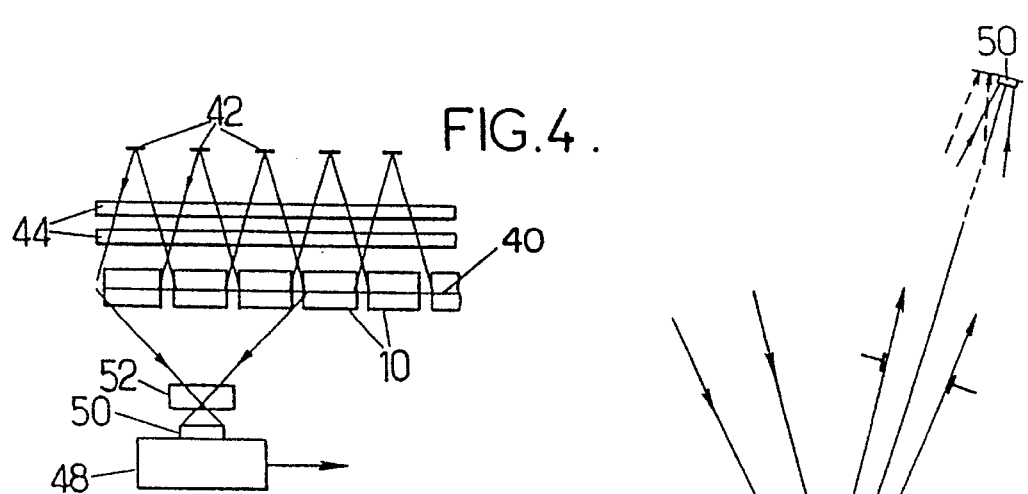
FIG. 4 shows, a possible arrangement of sources and of sensors allowing simultaneous classification of several pellets, as seen from the top of FIG. 3.

A device having the basic structure shown in FIG. 2, may be regarded as consisting of a certain number of components between which the various functions to be fulfilled are distributed. The distribution which will be given is in no way exclusive, neither are the items of equipment which will be given by way of example.

As represented, the device comprises a data-acquiring apparatus 20 having means 22 for receiving the pellets and for rotating these pellets, and an optical inspection unit 24. The means 22 for receiving the pellets and for rotating them may be controlled by a programmable controller 26. These means 22 may have the construction described in French Patent Application No. 92 15846 "Device for automatically sorting pellets", filed on Dec. 29, 1992 in the name of the same assignee as the present application. The controller 26 may then be provided for controlling the loading of the pellets onto the reception means 22, the rotating of the pellets, the unloading of the pellets and their distribution towards various receptacles depending on the classification.

The operation of the entire device may be controlled by a computer 28 having a data-input keyboard 29, a display screen 30 and a printer 32 for printing the results of the classification. The optical inspection unit 24 transmits the information via a link 34 to the preprocessing cards installed in a cabinet 36. The preprocessed information is transmitted to the computer 28. However, different distribution of functions would also be possible.

The optical inspection unit 24 may have the basic construction shown in FIGS. 3 and 4 when the device is intended for simultaneously classifying m×n=4×3=twelve pellets 10. It comprises an illumination assembly and an image-taking assembly.

The illumination assembly is intended to illuminate all twelve pellets along a very narrow straight line 40, typically about 50 μm wide. To this end, the illumination means may include twelve aligned laser diodes 42. The astigmatism of the beam emitted by a laser diode is sufficiently great to cover the entire length of a pellet, as shown in FIG. 4. A focal optics, consisting of cylindrical lenses 44, focus the beam in the form of a narrow line corresponding exactly to a generatrix on the surface of a pellet 10 of nominal diameter and not having any surface defects, as shown in FIG. 5.

The image-taking means, called sensors, include, in the case illustrated, at least one linear-type camera 48, generally having a CCD linear array 50, which can have a single row of detectors or several rows, with transfer from one line to another in synchronism with the rotational movement of the pellet. In all cases, the noise is advantageously reduced by charge storage. The optics 52 of the camera are such that the image of the line illuminated by the source 42 on a pellet of nominal diameter and having no three-dimensional defects is formed on the linear array 50. For example, in the above case of a device for simultaneously classifying twelve pellets, four aligned cameras each including a linear array of 1,728 detectors are provided. Each detector of the camera thus observes a square of 50 μm sides.

Figure 5:
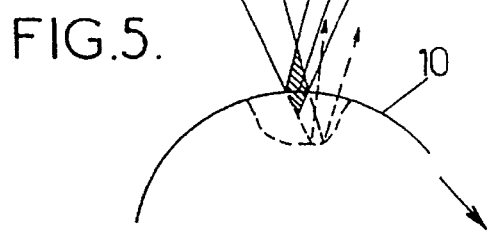
FIG. 5 shows schematically on a large scale, an illuminated pellet zone and the effect of a defect indicated by dashes.

FIG. 5 shows that each detector 50 receives only the light reflected or scattered in an intersection zone, indicated by hatching. This zone has the shape of a diamond, the elongation of which depends on the chosen angles of incidence and of observation. With an incidence away from the normal, a three-dimensional defect on a pellet of nominal diameter, such as the defect indicated by the dashes, reduces the light received by the sensor and may even reduce it to zero.

The optical inspection unit 24 is fitted with means making it possible to adjust its characteristics and, in most cases, means making it possible to adjust its position in relation to the device which carries the means 22 for receiving and rotating the pellets.

In the embodiment shown in FIG. 3, the means for mechanically adjusting the optical inspection unit are constituted by sets of nuts and screws, these being fitted with means allowing them to be locked.

These means include, for the sensors, means T1 for adjusting the position in relation to a baseplate 94 making it possible to select the angle of observation of the generatrices of a pellet 10 and means R1 for adjusting the orientation of the sensor. Focusing adjustment is performed with the aid of means H4, allowing the optics 52 to be moved along the optical axis. The means R1, T1, H4 therefore allow the image-taking means, called sensors, to be adjusted on the template.

The means for adjusting the illumination assembly 21 include means T2, R2 and T3 fulfilling a role similar to that of the means T1, R1 and H4. They make it possible to focus the illumination onto the template. The nut-and-screw set T3 makes it possible to focus the illumination of the observed generatrix.

The means H1, H2, H3, R3, T5 make it possible to adjust the optical inspection unit, previously calibrated, in relation to the means 22 for receiving and for rotating the pellets; in particular, the attitude and height adjustment of the optical inspection unit 24, on the frame 96 of the apparatus, may be constituted by a set of three micrometer screws H1, H2 and H3 arranged at the vertices of a triangle.

The means 22 generally also include adjustment means. In the case illustrated in FIG. 3, they include angular adjustment means R3, making it possible to adjust the orientation of the sensor in relation to the pellets, and linear adjustment means T5, allowing the line observed and illuminated by the optical inspection unit 24 to be brought into coincidence with an actual generatrix. The member T4 allows the device to be adjusted mechanically by construction.

The mechanical adjustment of the optical inspection unit is performed in the workshop, before it is installed onto the apparatus, by replacing the pellets 10 by a template or standard bearing a three-dimensional reference line and an additional line which is parallel to it. In order to adjust the optical inspection unit, it is arranged on the standard, in such a way that it illuminates the three-dimensional line. The position of the diodes is adjusted with the aid of adjustment screws, associated with a rotation-translation mechanism plate. In some cases (first adjustment, for example) a microscope may be used to accurately position the diodes.

After the adjustment of the diodes, the optical inspection unit is returned to the standard; the diodes then illuminate the second line. The cameras are switched on. The signal which they receive is displayed on a control monitor of the optical inspection unit. The geometrical positioning of the cameras is obtained by seeking the maximum point in the light signal. This is obtained by using the adjustments of the rotation mechanism plate in order to align perfectly the CCD linear array of the sensor and the zone illuminated by the diodes. The adjustments T1–R1 of the translation mechanism plate are used to center the linear array on the illuminated zone. Next, the objective of the camera is adjusted in order to focus the sensor onto the second line which represents the generatrix of the pellets to be observed.

The camera 48 (or each camera) is connected to an input of a preprocessing assembly having functions of acquisition of the information coming line by line from the cameras, of analog preprocessing of this information with selection of the potential defect zones, and of organization of the information, pellet by pellet, in the case where the camera receives signals from several pellets.

The processing assembly 51 shown schematically in FIG. 7 comprises two comparators 53 and 54 and a selection circuit 56 making it possible to separate the signals located in a normality region between two threshold levels V1 and V2 (FIG. 6) from those located outside the normality region. The thresholding at the levels V1 and V2 is advantageously implemented, scanning line by scanning line, from the start of the acquisition of the image of a pellet. The selection circuit 56 can, identify the normality points by a code and, can orient the abnormality points. The digital information thus obtained is grouped together, pellet by pellet, by an output circuit 60 and oriented, in the case represented, towards three identical processing circuits 62, which can be grouped together into a single integrated circuit and only one of which will be described. This processing may be performed by storing in memory the transitions between a normality region and an abnormality region, making it unnecessary to store in memory all the normality points. This storing in memory may be performed in a memory incorporated in the output circuit 60.

The operating strategy of each processing circuit, with a view to recognizing the defects and their significance, may includes the following steps:

registering each defect, its shape and its area by neighborhood analysis, with line-by-line dynamic reconstruction, analyzing the shape of the defect (area, elongation, roundness, etc.) with a view to its classification, identify the defect based on its average grey level and the previous information, classifying each defect and, classifying of the pellet according to the type, significance and position of its defects.

In particular, the equipment processes some cases of critical relative position of defects which, taken individually, are acceptable. Thus, the device according to the invention makes it possible to detect ungulate defects 19 liable to cause a chip such as 12, by propagation of the cracks, when the pellet is loaded into the rod.

The processing circuit 62 shown in FIG. 7 comprises a first processor 64 associated with a RAM having a capacity at least equal to that of two scanning lines. This processor compares each line of order n with the previous line of order n−1 so as to determine whether a defect existing on the line n−1 still exists on the line n: it may thus supply, on its output 68, information relating to the geometry of the defect and the average grey level of the defect to a buffer memory 70. The contents of this buffer memory are processed by a second processor 72 as soon as the first processor 64 sends a signal indicating that a defect is completely represented in the memory 70. As it is possible to have several separate defects on the same scanning line, the processor 64 is designed to be able to process several defects at the same time.

The role of the processor 72 is especially to identify the type of defect using new thresholding, applied to the average grey level of this defect over the entire extent of this defect, following the complete formation of the image. This thresholding is performed at digital levels corresponding to thresholds V3 and V4 (FIG. 6) located on either side of the normality region. The thresholds V1, V2, V3 and V4 are advantageously adjustable, for example in the course of a prior calibration performed using either a standard pellet passed as sound or having defects calibrated according to type and significance, or using a simple linear array.

Figure 6:
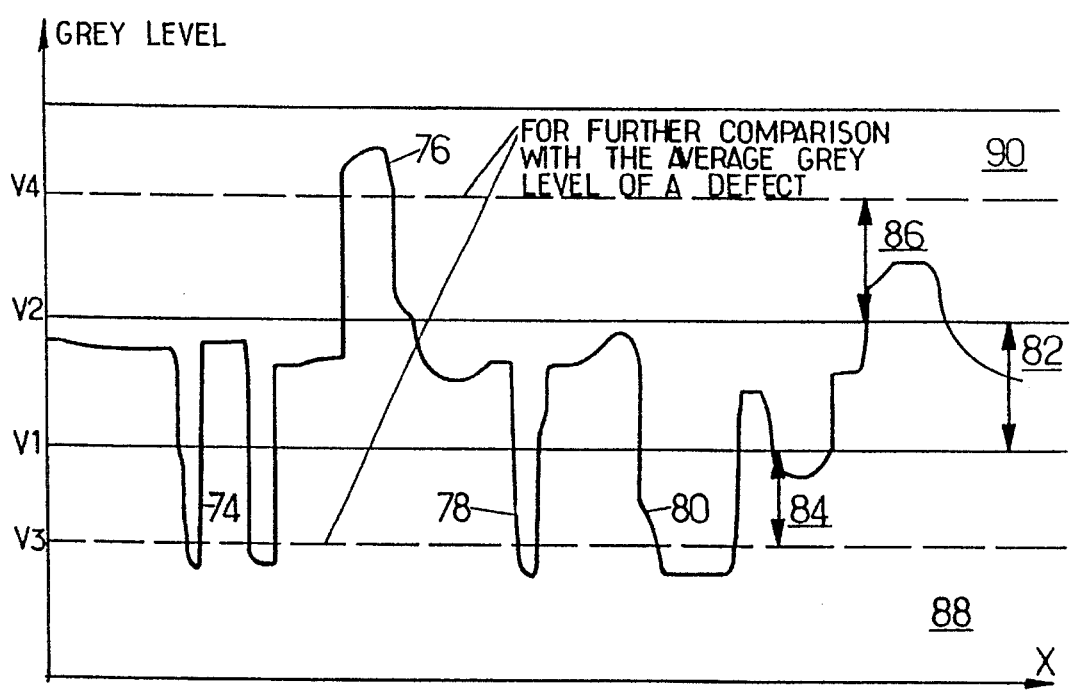
FIG. 6 is a linear diagram showing a possible variation in the signal during the integration over a generatrix having various defects.

FIG. 6 shows a signal shape which may be considered as typical when scanning a line having, in succession, along the length L of the pellet, a pit 74, an inclusion or a grinding defect 76, a crack 78 and a chip 80. The zone 82 corresponds to the normal grey level. The regions 84 and 86 correspond to dark and light spots. The region 88 corresponds to three-dimensional defects. The zone 90 corresponds to grinding defects or to inclusions.

The processor 72 thus differentiates surface defects from three-dimensional defects by means of the thresholding operation. In addition, it includes artificial intelligence, stored in memory, in the form of a program and a parameter list, making it possible to identify the type of three-dimensional defect according to its shape and its extent. Numerous artificial intelligence systems are already known which make it possible to sort defects as a function of geometrical and reflectivity characteristics of these defects: reference may be made especially to the French patent application already mentioned and to the paper "Automatic classification of defects in semi-conductor devices", Dralla et al., in SPIE Vol. 1261, Integrated Circuit Metrology Inspection and Process Control IV (1990), pages 173 et seq. The stored artificial intelligence system may be provided for classifying each defect detected into three classes, A (defects sufficiently minute to be acceptable in all cases), B (defects acceptable for regions of the reactor not subjected to much stress), and R (defect unacceptable per se).

This information is transmitted by a final processor 92 which stores all the information relating to each pellet in turn and enables these pellets to be sorted. The pellets may be especially distributed into three classes:

pellets accepted because they do not have any defects or have only one A-type defect or at most a few A-type defects but not in penalizing combinations;

pellets which can be used in an environment not subjected to much stress because they have at most a few A or B-type defects which are not in unfavorable combinations;

pellets rejected because they include one or more R-type defects or an excessive number of A or B-type defects, or critical combinations of A or B-type defects.

It may be seen that the process makes it possible to reject a pellet as soon as an R-class defect appears and to stop the processing of this pellet from that moment, thereby saving computation time. Not only are the defects identified, but their characteristics are determined and stored, so that it is possible to take into account not only the seriousness of each defect, but also other factors, such as the relative position of several defects which may lead to the pellet being rejected or being assigned to class B, although the individual defects are minor.

It is possible to adopt a sequence of steps other than that given hereinabove by way of example. However, as a general rule, there will be, in succession:

identification of the defects by neighborhood analysis, i.e., morphology processing on neighborhoods, and analysis of the grey levels;

classification of the individual defects, with rejection as soon as a defect appears which is unacceptable per se; and classification of the pellet.

By way of example, it may be mentioned that a device has been produced for processing twelve pellets at the same time. The optical inspection unit incorporates 12 laser diodes and supplies a line of light 300 millimeters in length and 50 µm in width. The laser diodes have the advantage of low electrical consumption (4 watts to supply a light power of 36 milliwatts). The rotational drive mechanism enables each pellet to be rotated on itself through one revolution in less than one second. Each camera is designed to record the light energy on each detector by successive steps of 50 µm, each sensor having a transverse field of 50 µm. Thus, any defect having an area at least equal to $100 \times 100$ µm$^2$ is detectable with 80% probability. The processing of the information allows correct measurement of the size of a defect above an area of $250 \times 250$ µm$^2$ to be provided.

The invention also proposes a construction which allows convenient and accurate adjustment of the focusing onto the pellets and of the field of the cameras.

Another advantage of the device is that it enables the defects to be indexed by category and, if significant discrepancies occur in relation to one type of defect, to intervene rapidly in the manufacturing process in order to remedy this situation.

We claim:

1. Method for automatically classifying cylindrical nuclear-fuel pellets, said method comprising the steps of:

(a) rotating each pellet to be classified about its axis;

(b) focusing a flat beam coming from a light source onto a nominal generatrix of each said pellet, while said pellet is rotated;

(c) collecting returned light coming from an elongate zone which would be the zone illuminated on a defect-free pellet of nominal diameter;

(d) detecting reflected light intensity, point by point, along said elongate zone; and (e) deriving defects from variations in said light intensity by:

(i) determining those of said points in each zone from which the intensity of returned light lies between an adjustable upper normality threshold and an adjustable lower normality threshold;

(ii) storing transitions between a normality region and an abnormality region and storing the intensity, in digital form, for only those of said points which are in the abnormality region;

(iii) determining limits of each said defect by neighborhood analysis of determining a nature of the defect among predetermined natures of defect, each nature being identified by geometrical criteria and average-light-intensity criteria of said defect; and (iv) classifying the pellets by assigning each of said pellets to a class selected between at least one class of correct pellets and one class of rejected pellets, depending on a said nature of defect, steps (a) to (e) being carried out only once per pellet;

wherein step (e) includes successively storing the intensities of all points of the abnormality region and performing a type-discrimination thresholding, having two additional threshold levels away from a normality zone defined by said upper normality threshold and lower normality threshold, on an average grey level of each defect detected.

2. Method according to claim 1, wherein the discrimination thresholding is performed using software, after digitizing the intensity.

3. Method for automatically classifying cylindrical nuclear-fuel pellets, said method comprising the steps of:

(a) rotating each pellet to be classified about its axis;

(b) focusing a flat beam coming from a light source onto a :nominal generatrix of each said pellet, while said pellet is rotated;

(c) collecting returned light coming from an elongate zone which would be the zone illuminated on a defect-free pellet of nominal diameter;

(d) detecting reflected light intensity, point by point, along said elongate zone; and (e) deriving defects from variations in said light intensity by:

(i) determining those of said points in each zone from which the intensity of the returned light lies between an adjustable upper normality threshold and an adjustable lower normality threshold;

(ii) storing transitions between a normality region and an abnormality region and storing the intensity, in digital form, for only those of said points which are in the abnormality region;

(iii) determining limits of each said defect by neighborhood analysis and determining a nature of the defect among predetermined natures of defect, each nature being identified by geometrical criteria and, average-light-intensity criteria of said defect; and (iv) classifying the pellets by assigning each of said pellets to a class selected between at least one class of correct pellets and one class of rejected pellets, depending on a said nature of defect, steps (a) to (e) being carried out only once per pellet.

4. Method according to claim 3, wherein the type and significance of the defects is determined by artificial intelligence using a dynamic reconstruction of the extent of the defects.

5. Optical device for automatically inspecting cylindrical nuclear-fuel pellets, said device comprising:

(a) a light source for focusing a beam in the form of a line along a generatrix of a pellet to be inspected;

(b) means for receiving at least one pellet and for rotating said pellet on itself about its axis;

(c) a light sensor having a linear array of individual detectors on which an image of the illuminated generatrix of the pellet is formed by lens means, rotation of said pellet allowing all generatrices of said pellet to be scanned; and (d) a signal processor connected to receive an output of said sensor, said signal processor comprising:

(i) a preprocessing unit for determining those output signals from the detectors which are outside a normality region defined by an adjustable upper threshold and an adjustable lower threshold, and for detecting transition zones along each of said generatrices which return signals in said end zones outside said normality region;

(ii) at least one processing circuit for reconstructing defects, line by line, by comparing each line with a succeeding line and identifying a nature of each of said defects by its shape and its color level or grey level; and (iii) means for storing all the defects in memory, as said pellet is being scanned, and for classifying said pellet as a function of a number and nature of the detected defects, said signal processor being arranged to reconstruct said defect and classifying each said pellet responsive to said output signals providing a single representation of each of said pellets.

6. Device according to claim 5, wherein the device is designed to receive n×m pellets simultaneously, n and m being integers greater than 1, and rotationally drive them simultaneously and in synchronism and comprises n sensors each having m×p said detectors, one said preprocessing unit performing the comparison with the normality thresholds for the signals supplied by said m×p detectors and distributing them between n×m said processing circuits.

7. Device according to claim 5, wherein the light source belongs to an illumination assembly fitted with mechanical means for focusing the illumination onto a first line of a template.

8. Device according to claim 5, wherein the sensor is fitted with means making it possible to adjust its focusing in correspondence with the illumination onto a second line of a template.

9. Optical device according to claim 5, wherein said signal processor is arranged to identify said nature of each said defect by applying an additional thresholding step to an average gray level of the defect over an entire extent of the defect.

10. Device according to claim 5, wherein said signal processor is arranged to compare each line of order n-1 where one said defect exists with a line of order n so as to determine whether the defect existing in line n−1 still exists on line n.

11. Device according to claim 5, wherein said processing circuit includes a first processor arranged for storing information relating to the full geometry of each of said defects in turn in a memory and a second processor for identifying each said defect after it has been completely represented in said memory.

* * * * *